(12) United States Patent
Olson (10) Patent No.: US 11,464,417 B2
(45) Date of Patent: Oct. 11, 2022

(54) SYSTEM AND METHOD FOR SORTING ELECTRO-PHYSIOLOGICAL SIGNALS FROM MULTI-DIMENSIONAL CATHETERS

(71) Applicant: St. Jude Medical, Cardiology Division, Inc., St. Paul, MN (US)

(72) Inventor: Eric S. Olson, Maplewood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 307 days.

(21) Appl. No.: 16/645,754

(22) PCT Filed: Jul. 12, 2018

(86) PCT No.: PCT/US2018/041852
§ 371 (c)(1),
(2) Date: Mar. 9, 2020

(87) PCT Pub. No.: WO2019/055115
PCT Pub. Date: Mar. 21, 2019

(65) Prior Publication Data
US 2020/0268259 A1  Aug. 27, 2020

Related U.S. Application Data

(60) Provisional application No. 62/559,753, filed on Sep. 18, 2017.

(51) Int. Cl.
*A61B 5/0245* (2006.01)
*A61B 5/0538* (2021.01)
(Continued)

(52) U.S. Cl.
CPC .......... *A61B 5/0245* (2013.01); *A61B 5/0538* (2013.01); *A61B 5/063* (2013.01);
(Continued)

(58) Field of Classification Search
None
See application file for complete search history.

(56) References Cited

U.S. PATENT DOCUMENTS 5,697,377 A   12/1997 Wittkampf
5,983,126 A   11/1999 Wittkampf
(Continued)

FOREIGN PATENT DOCUMENTS

EP    3192442      7/2017
WO   2007/146864  12/2007

OTHER PUBLICATIONS

International Search Report and Written Opinion for PCT/US2018/041852, dated Oct. 4, 2018.
(Continued)

*Primary Examiner* — Ankit D Tejani
(74) *Attorney, Agent, or Firm* — Wiley Rein LLP (57) ABSTRACT

A plurality of electrophysiological signals measured by a respective plurality of electrodes carried by a multi-dimensional catheter can be sorted relative to a direction of interest, such as a cardiac activation wavefront direction. An electroanatomical mapping system can be used to determine the orientation of the multi-dimensional catheter relative to the direction of interest. For example, the user can manually adjust the orientation by manipulating a slider, a wheel, or a similar graphical user interface control. As another example, the user can draw a presumed orientation on a geometric model. Once the orientation is determined, the system can sort the plurality of electrophysiological signals and output a graphical representation of the sorted plurality of electrophysiological signals, for example as a plurality of traces.

13 Claims, 7 Drawing Sheets

(51) Int. Cl.
  *A61B 5/06* (2006.01)
  *A61B 5/00* (2006.01)
  *A61B 5/287* (2021.01)
  *A61B 5/339* (2021.01)
  *A61B 5/349* (2021.01)

(52) U.S. Cl.
  CPC .............. *A61B 5/287* (2021.01); *A61B 5/339* (2021.01); *A61B 5/349* (2021.01); *A61B 5/6852* (2013.01); *A61B 5/72* (2013.01); *A61B 5/743* (2013.01)

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,720,520 B2 * | 5/2010 | Willis .................... A61B 90/36 600/374 |
| 7,885,707 B2 | 2/2011 | Hauck |
| 8,577,450 B1 | 11/2013 | Chmiel et al. |
| 10,105,074 B2 | 10/2018 | Serevino |
| 2002/0026220 A1 | 2/2002 | Groenewegen et al. |
| 2002/0053870 A1 | 5/2002 | Panescu et al. |
| 2007/0287902 A1 | 12/2007 | Fuimaono et al. |
| 2007/0299353 A1 * | 12/2007 | Harlev .................... A61B 5/287 600/509 |
| 2010/0324414 A1 | 12/2010 | Harlev et al. |
| 2011/0160593 A1 | 6/2011 | Deno et al. |
| 2012/0184863 A1 | 7/2012 | Harlev |
| 2013/0041243 A1 | 2/2013 | Byrd et al. |
| 2013/0131529 A1 | 5/2013 | Jia et al. |
| 2015/0119738 A1 | 4/2015 | Deno |
| 2015/0228254 A1 | 8/2015 | Olson |
| 2017/0055864 A1 | 3/2017 | Han et al. |
| 2020/0268259 A1 | 8/2020 | Olson |

OTHER PUBLICATIONS

Deno et al., "Orientation-Independent Catheter-Based Characterization of Myocardial Activation" IEEE Transactions on Biomedical Engineering, vol. 64, No. 5, May 2017, pp. 1067-1077.

Massé et al., "Resolving Myocardial Activation With Novel Omnipolar Electrograms," Circulation: Arrhythmia and Electrophysiology, vol. 9, issue 7, Jul. 2016.

\* cited by examiner

SYSTEM AND METHOD FOR SORTING ELECTRO-PHYSIOLOGICAL SIGNALS FROM MULTI-DIMENSIONAL CATHETERS

CROSS-REFERENCE TO RELATED APPLICATIONS

The instant application claims the benefit of U.S. provisional application No. 62/559,753, filed 18 Sep. 2017, which is hereby incorporated by reference as though fully set forth herein.

BACKGROUND

The present disclosure relates generally to cardiac diagnostic and therapeutic procedures, such as electrophysiological mapping and cardiac ablation. In particular, the present disclosure relates to systems, apparatuses, and methods for sorting electrophysiological signals measured by multi-dimensional catheters, such as high density ("HD") grid catheters.

It is known to visualize electrode traces (e.g., intracardiac electrogram traces) measured using an electroanatomical mapping system. For example, the traces can be stacked vertically on a display, with the order of the traces corresponding to the order of electrodes on the electrophysiology catheter. This approach to displaying electrode traces is logical for electrophysiology catheters that include electrodes arranged along a single axis, because linear catheters provide a natural sorting direction along the catheter spline (e.g., most proximal to most distal or vice versa).

With the increased usage of electrophysiology catheters that include electrodes arranged along multiple axes and/or in two- or three-dimensions, such as HD grid catheters, pentarray catheters, and/or spiral catheters, however, the approach described above may not be as logical.

BRIEF SUMMARY

Disclosed herein is a method of sorting a plurality of electrophysiological signals measured by a respective plurality of electrodes carried by a multi-dimensional catheter. The method includes: determining, via an electroanatomical mapping system, an orientation of the multi-dimensional catheter relative to a direction of interest (e.g., a cardiac activation wavefront direction); and sorting, via the electroanatomical mapping system, the plurality of electrophysiological signals using the orientation of the multi-dimensional catheter relative to the direction of interest. The method can also include the electroanatomical mapping system outputting a graphical representation of the sorted plurality of electrophysiological signals.

According to aspects of the disclosure, the step of determining, via an electroanatomical mapping system, an orientation of the multi-dimensional catheter relative to a direction of interest the electroanatomical mapping system includes generating a graphical user interface and receiving a user selection of the orientation through the graphical user interface. For example, the graphical user interface can include an orientation selection wheel, an orientation selection slider, or another virtual control to select the orientation.

Alternatively, the user's definition of a presumed cardiac activation wavefront direction can be received through the graphical user interface, such as by receiving the user's definition of a cardiac activation wavefront direction on a geometric model of a heart.

It is also contemplated that the method can include outputting a graphical representation of the user selection of the orientation on a geometric model of a heart.

In other aspects of the disclosure, the step of determining, via an electroanatomical mapping system, an orientation of the multi-dimensional catheter relative to a direction of interest includes the electroanatomical mapping system determining the cardiac activation wavefront direction from the plurality of electrophysiological signals.

The step of sorting, via the electroanatomical mapping system, the plurality of electrophysiological signals using the orientation of the multi-dimensional catheter relative to the direction of interest can include: computing, via the electroanatomical mapping system, a rotation matrix using the orientation of the multi-dimensional catheter relative to the direction of interest; applying the rotation matrix, via the electroanatomical mapping system, to a respective plurality of positions of the plurality of electrodes; sorting the plurality of electrophysiological signals according to the respective plurality of positions of the plurality of electrodes after applying the rotation matrix thereto.

Also disclosed herein is a method of determining a sequence in which a cardiac activation wavefront passes through a plurality of electrodes carried by a multi-dimensional catheter, including: determining, via an electroanatomical mapping system, an orientation of the multi-dimensional catheter relative to a direction of the cardiac activation wavefront; and determining the sequence in which the cardiac activation wavefront passes through the plurality of electrodes using the orientation of the multi-dimensional catheter relative to the direction of the cardiac activation wavefront.

The step of determining, via an electroanatomical mapping system, an orientation of the multi-dimensional catheter relative to a direction of the cardiac activation wavefront can include: displaying a plurality of traces corresponding to a plurality of electrophysiological signals respectively measured by the plurality of electrodes; the electroanatomical mapping system generating a graphical user interface and receiving a user selection of a presumed orientation through the graphical user interface; the electroanatomical mapping system re-sorting the displayed plurality of traces using the presumed orientation.

The graphical user interface can include an orientation adjustment wheel, an orientation adjustment slider, or a similar virtual control.

Alternatively, the step of receiving a user selection of a presumed orientation through the graphical user interface can include receiving a user's definition of a presumed conduction velocity vector through the graphical user interface.

In other aspects of the disclosure, the step of determining, via an electroanatomical mapping system, an orientation of the multi-dimensional catheter relative to a direction of the cardiac activation wavefront includes the electroanatomical mapping system determining the direction of the cardiac activation wavefront direction from a plurality of electrophysiological signals respectively measured by the plurality of electrodes.

The instant disclosure also provides a system for sorting a plurality of electrophysiological signals measured by a respective plurality of electrodes carried by a multi-dimensional catheter, the system including a sorting and visualization module configured to: determine, using information received by an electroanatomical mapping system, an orientation of the multi-dimensional catheter relative to a direction of interest; and sort the plurality of electrophysiological signals using the orientation of the multi-dimensional catheter relative to the direction of interest. The system can also include a user interface module configured to receive as input a user selection of the orientation through a graphical user interface, which can in turn include a geometric model of a heart.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for sorting electrophysiological signals measured using a multi-dimensional catheter. For purposes of illustration, aspects of the disclosure will be described with reference to sorting electrophysiological signals measured using an HD grid catheter according to the direction of travel of a cardiac activation wavefront relative to the electrodes carried by the HD grid catheter. It should be understood, however, that the teachings herein can be applied to good advantage in other contexts and/or with respect to other electrode configurations.

Figure 1:
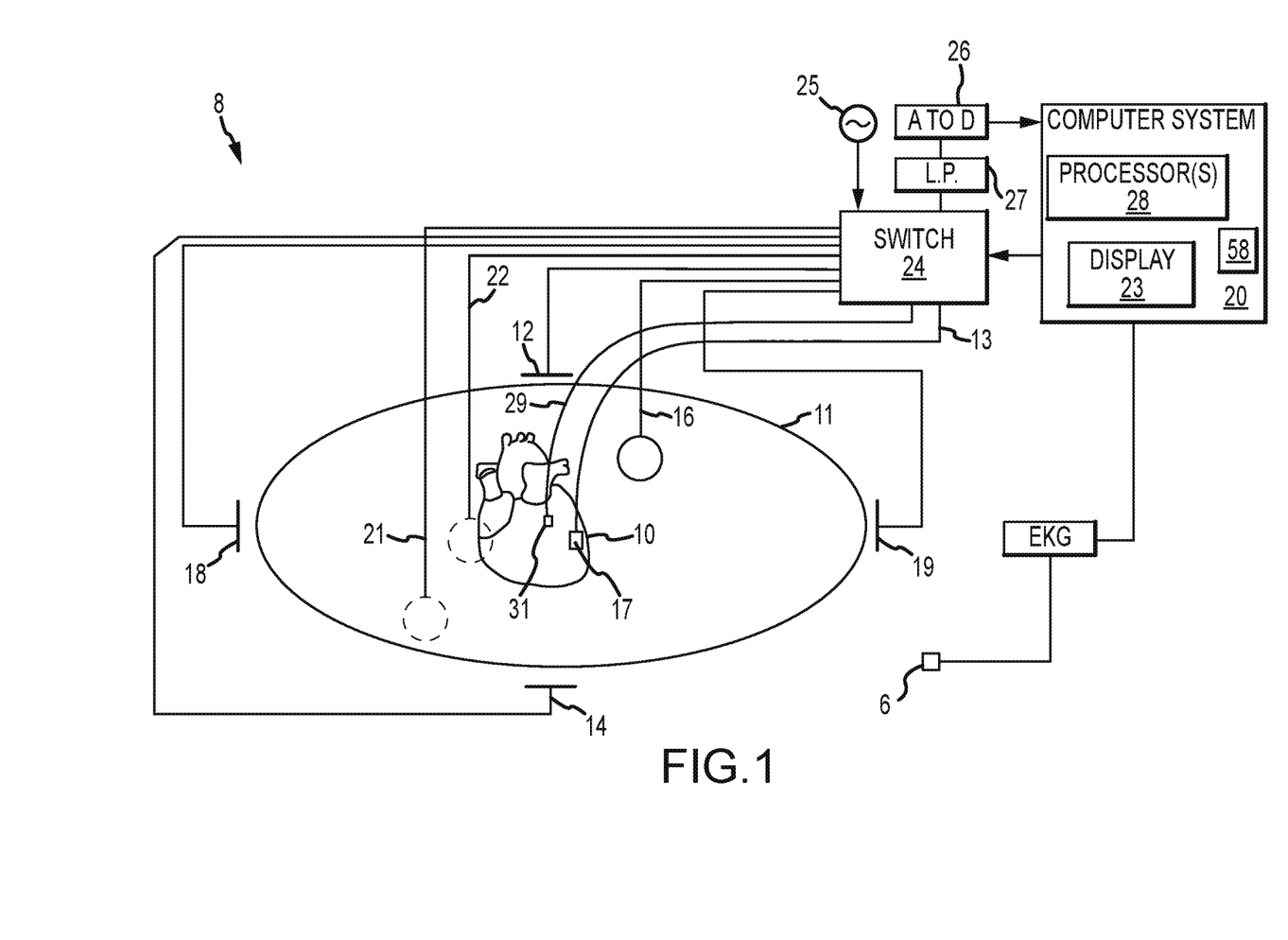
FIG. 1 is a schematic diagram of an exemplary electro-anatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
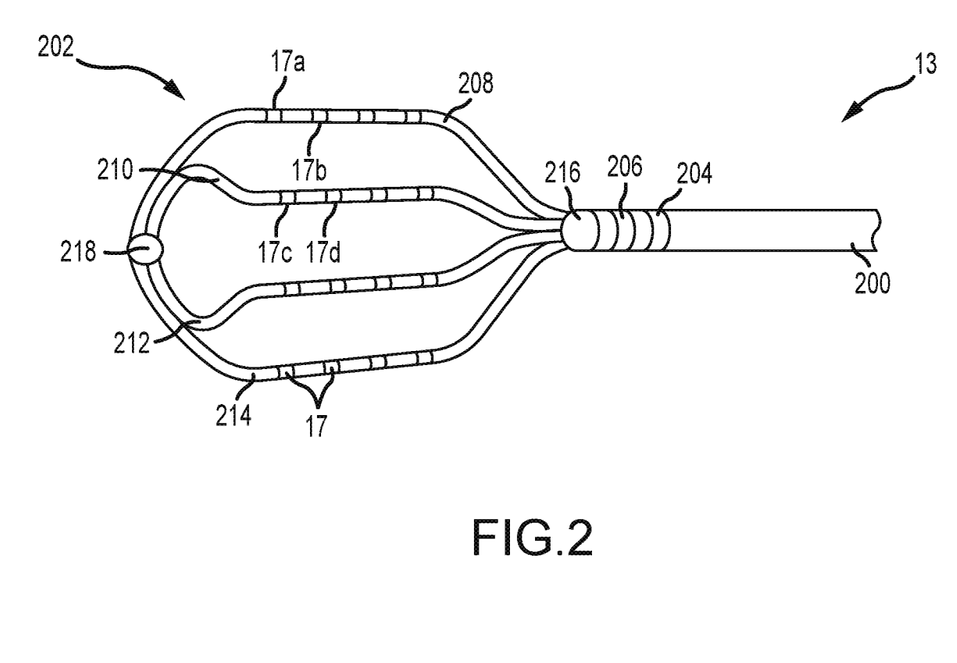
FIG. 2 depicts an exemplary catheter that can be used in connection with aspects of the instant disclosure.

In particular, for purposes of this disclosure, a segment of an exemplary multi-electrode catheter 13, often referred to as an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers and using familiar procedures. Indeed, various approaches to introduce catheter 13 into the left ventricle of the patient's heart 10, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to the sorting of electrophysiological signals, for example in order to display graphical representations (e.g., traces) thereof on display 23. System 8 can therefore also include a sorting and visualization module 58 that can be used to sort and generate graphical representations (e.g., traces) of electrophysiological signals on display 23. Those of ordinary skill in the art will be familiar with the graphical representation of electrophysiological signal traces in conjunction with electroanatomical mapping systems, such that a detailed description of the same is not necessary to an understanding of the instant disclosure.

Figure 3:
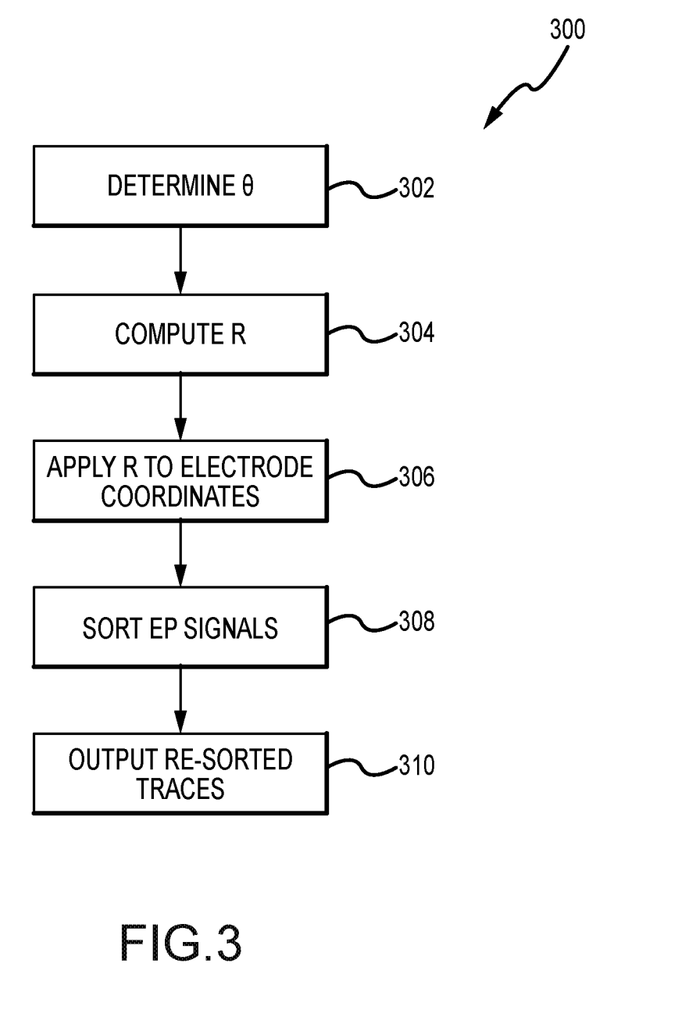
FIG. 3 is a flowchart of representative steps that can be followed according to exemplary embodiments disclosed herein.

One exemplary method of sorting and visualizing electrophysiological signals according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or sorting and visualization module 58). It should be understood that the representative steps described below can be either hardware- or software-implemented. For the sake of explanation, the term "signal processor" is used herein to describe both hardware- and software-based implementations of the teachings herein.

Figure 4:
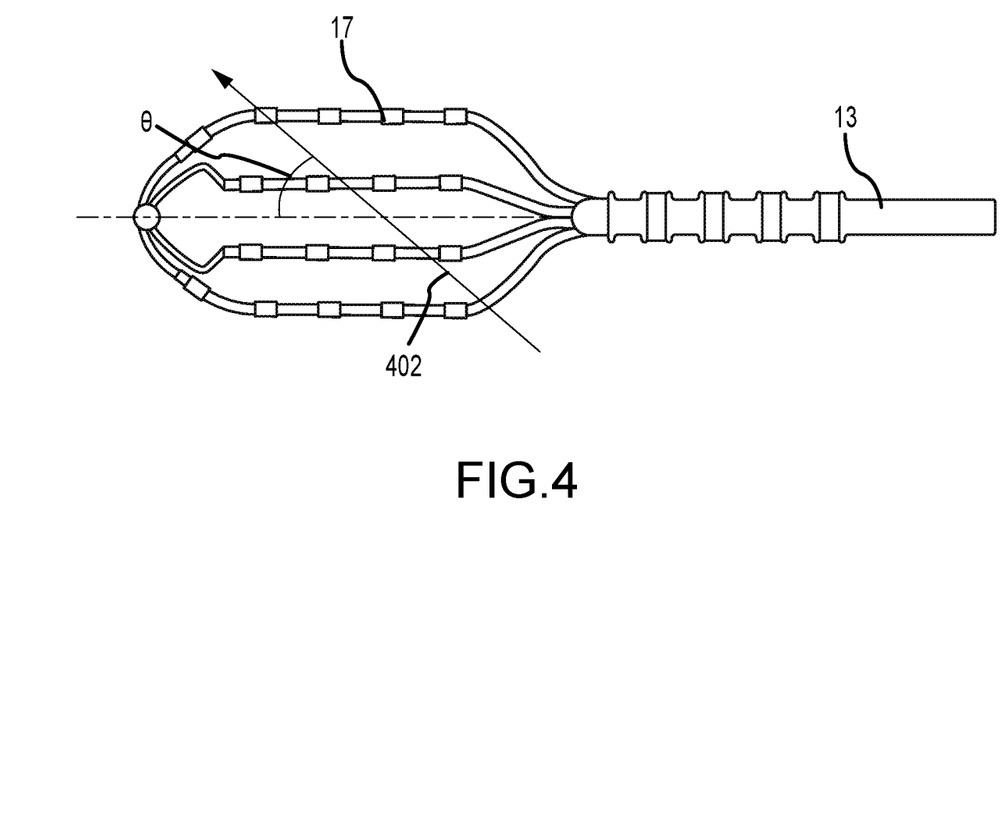
FIG. 4 depicts the angle Θ between the multi-electrode catheter of FIG. 2 and a direction of interest, such as a cardiac activation wavefront direction.

In block 302, system 8 determines the orientation of catheter 13 relative to a direction of interest 402, represented by an angle Θ shown in FIG. 4. Embodiments of the disclosure relate to sorting the plurality of electrodes 17 (e.g., 17a, 17b, 17c, 17d, etc.) with respect to the direction of interest. For purposes of explanation herein, direction of interest 402 will be the direction of the cardiac activation wavefront, and the sorting will be the order in which the cardiac activation wavefront passes through the plurality of electrodes 17.

Figure 5A:
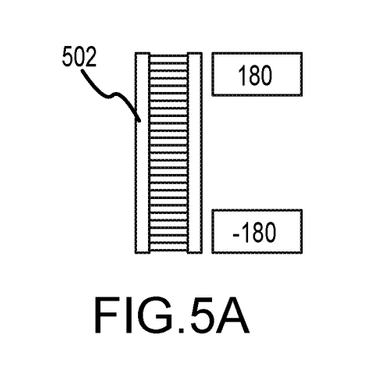
FIGS. 5A-5C depict various graphical user interfaces ("GUI") through which a practitioner can adjust the angle Θ.
Figure 5B:
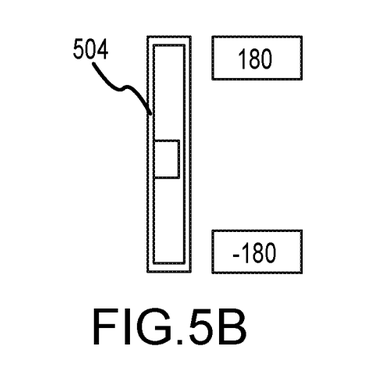

Various approaches to determining the orientation of catheter 13 relative to the direction of the cardiac activation wavefront are contemplated. In some embodiments of the disclosure, system 8 generates a graphical user interface through which a practitioner can specify the orientation. For example, system 8 can display an orientation selection control, such as a wheel 502 (FIG. 5A) or slider 504 (FIG. 5B) that allows the practitioner to adjust the orientation of catheter 13 relative to the direction of a hypothesized cardiac activation wavefront between 180° and −180° (for purposes of this disclosure, catheter 13 will be deemed to be oriented at 0° to the direction of the cardiac activation wavefront when the cardiac activation wavefront passes parallel to the length of catheter body 200 in a proximal-to-distal direction).

Figure 5C:
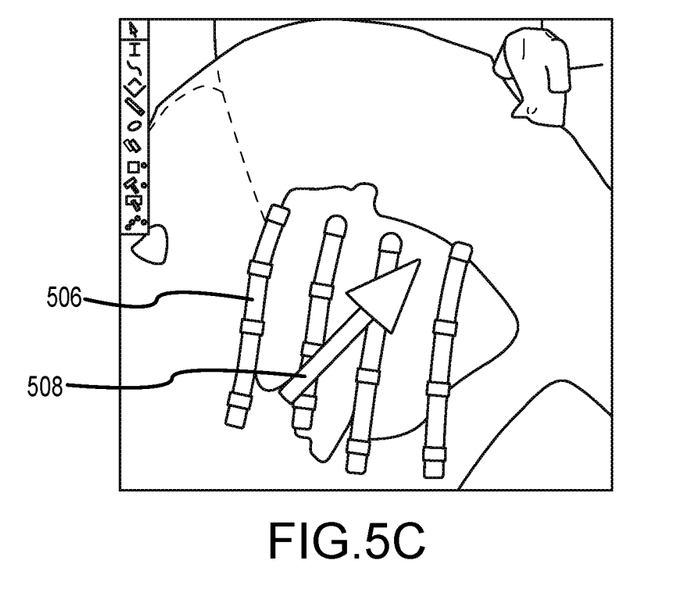

As another example, shown in FIG. 5C, system 8 can display a three-dimensional model 506 of catheter 13. The practitioner can draw (and, if necessary, adjust the direction of) an arrow 508 on model 506, where arrow 508 represents a presumed cardiac activation wavefront direction. In FIG. 5C, catheter 13 is oriented at approximately −45° to the presumed direction of the cardiac activation wavefront represented by arrow 508.

Figure 6A:
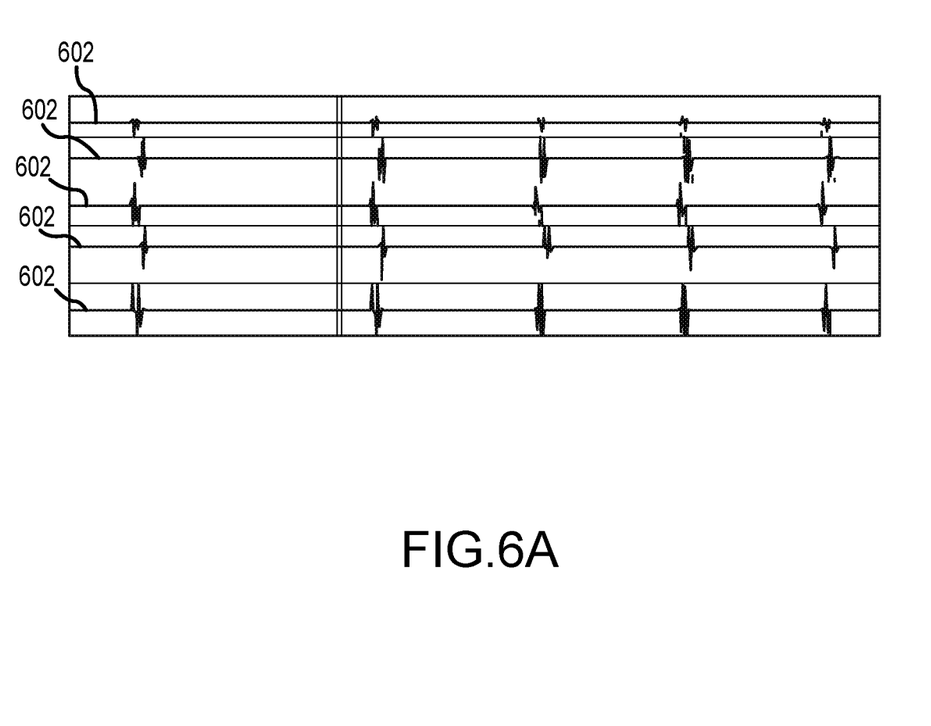
FIGS. 6A and 6B depict representative traces, both unsorted (FIG. 6A) and sorted according to the teachings herein (FIG. 6B).
Figure 6B:
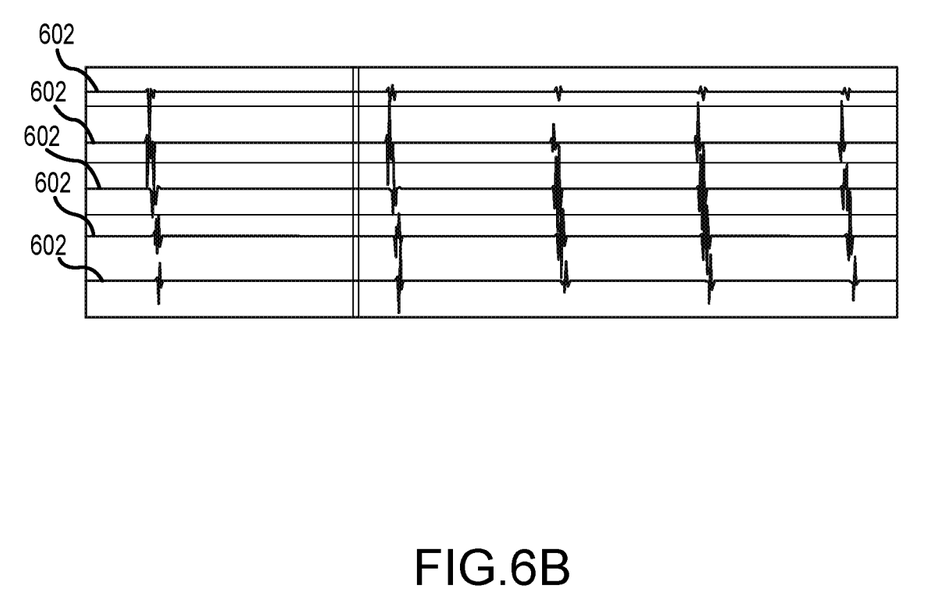

Use of the foregoing graphical user interfaces will be further described with reference to FIGS. 6A and 6B. A plurality of traces 602, representing bipolar electrogram signals measured using electrodes 17, are shown in each of FIGS. 6A and 6B. Those of ordinary skill in the art will appreciate that catheter 13 of FIG. 2 can measure a total of sixteen unipolar electrophysiological signals, and can thus generate a total of sixteen traces, though only five of them are depicted in FIGS. 6A and 6B for clarity of illustration. Those of ordinary skill in the art will also appreciate that numerous bipolar electrophysiological signals can also be constructed from the sixteen unipolar signals.

As will be appreciated by those of ordinary skill in the art, traces 602 are often updated on display 23 in real time (that is, they reflect the current beat). According to aspects of the instant disclosure, however, the practitioner can opt to freeze traces 602 on display 23, such that they no longer update in real time, but instead reflect the beat current at the time the freeze option was selected. An exemplary set of frozen traces 602 is shown as FIG. 6A. In FIG. 6A, however, traces 602 are not arranged logically relative to the cardiac activation wavefront direction (e.g., they are not sorted according to the order in which the cardiac activation wavefront passes through electrodes 17).

The graphical user interfaces disclosed herein (e.g., wheel 502, slider 504, and/or arrow 508) allow a practitioner to quickly test multiple possible sortations of electrodes 17 to determine which is best suited to the cardiac activation wavefront direction (e.g., which sortation corresponds most closely to the order in which the cardiac activation wavefront passes through electrodes 17). As the user manipulates the interface to adjust the angle Θ between the orientation of catheter 13 and the cardiac activation wavefront direction, electrodes 17 can be re-ordered to correspond to the newly-selected orientation (e.g., as discussed in further detail below) and their related traces 602 can be rearranged on display 23, until the practitioner identifies the most logical sortation (see, e.g., FIG. 6B). The practitioner can then opt to unfreeze the traces on display 23, so that they return to updating in real time, albeit sorted into an order better suited to the direction of the cardiac activation wavefront.

In other embodiments of the disclosure, the direction of interest, and therefore the angle Θ, can be determined analytically or computationally. For example, U.S. application no. 62/478,377, which is hereby incorporated by reference as though fully set forth herein, describes systems and methods for mapping local conduction velocity, including determining the direction of a cardiac activation wavefront. U.S. patent application publication no. 2017/0055864, which is also hereby incorporated by reference as though fully set forth herein, describes additional systems and methods for identifying and mapping cardiac activation wavefronts.

When the direction of the cardiac activation wavefront is determined analytically or computationally, the orientation of catheter 13 relative thereto can be determined using the equation $$\theta = \cos^{-1}\left(\frac{X \cdot \hat{v}}{|X||\hat{v}|}\right),$$

where X is the direction of catheter 13 (e.g., as determined by the measured positions of electrodes 17) and $\hat{v}$ is the direction of the conduction velocity vector (e.g., as analytically or computationally determined).

The orientation of catheter 13 relative to the cardiac activation wavefront direction (that is, the angle Θ) determined in block 302 can then be used to re-sort the electrophysiological signals measured by electrodes 17. In particular, in block 304, the orientation determined in block 302 is used to compute a rotation matrix R. More particularly, the rotation matrix R can be of form $$R = \begin{bmatrix} \cos\theta & -\sin\theta \\ \sin\theta & \cos\theta \end{bmatrix}.$$

In block 306, the rotation matrix R is applied to the nominal positions of electrodes 17 to compute rotated coordinates for electrodes 17. The nominal positions of electrodes 17 can be measured by system 8 and/or determined from the known geometry of catheter 13.

In block 308, the rotated electrode coordinates are used to re-sort the electrophysiological signals. According to a first aspect of the disclosure, electrodes 17 are re-ordered according to their rotated y coordinates (e.g., in order of increasing or decreasing rotated y coordinates). The same order can be applied to the corresponding electrophysiological signals, which can be output as traces 602 on display 23 according to familiar techniques in block 310.

In another aspect of the disclosure, the rotated y coordinates of the electrodes are used to compute the y-axis positions of the respective traces 602 on display 23. For example, the initial on-screen y-axis position (denoted $y_s$) of a trace 602 for a given electrode 17 having a rotated y coordinate of $y_e$ can be computed according to the equations $$a = \frac{(y_e - y_{e,min})}{(y_{e,max} - y_{e,min})} \text{ and}$$

$$y_s = a(y_{s,max} - y_{s,min}) + y_{s,min},$$

where $y_{e,max}$ and $y_{e,min}$ are, respectively, the maximum and minimum rotated y coordinates of the electrodes 17 and $y_{s,max}$ and $y_{s,min}$ are, respectively, the maximum and minimum on-screen y-axis positions within which traces 602 are to be displayed. The initial y-axis positions of traces 602 can then be uniformly redistributed between $y_{s,max}$ and $y_{s,min}$ and traces 602 can be output on display 23 in block 310.

In embodiments of the disclosure where the cardiac activation wavefront direction is computationally or analytically determined (and thus where Θ is computationally or analytically determined), the electrophysiological signals and their respective traces can be re-sorted on a beat-by-beat basis. Alternatively, the electrophysiological signals and their respective traces can be re-sorted "on demand" (e.g., when the practitioner desires re-sorting). According to aspects of the disclosure, system 8 can provide an alert to a practitioner (e.g., visual and/or audible signals) when the current sorting of electrophysiological signals is no longer optimal. For example, one form of visual signal is that traces 602 will appear "out of order" (e.g., similar to FIG. 6A). Another form of visual signal is to color traces 602 differently (e.g., drawn in red instead of green) when they are not optimally sorted.

Although several embodiments have been described above with a certain degree of particularity, those skilled in the art could make numerous alterations to the disclosed embodiments without departing from the spirit or scope of this invention.

For example, once the cardiac activation wavefront direction is determined (e.g., by the user prescribing the waveform sorting direction), the wavefront direction can be graphically represented on display 23, such as by drawing an arrow on a three-dimensional model of the heart, in a manner similar to that illustrated in FIG. 5C. By drawing several such arrows on the three-dimensional model with catheter 13 at several locations within the heart, one can create a cardiac activation wavefront map that can be useful, for example, in visualizing errant conduction pathways.

As another example, the traces can be resorted without freezing the display. For example, according to aspects of the disclosure, the sortation can be triggered to an ECG signal.

As still another example, the teachings herein are applicable not only to impedance-based localization systems (such as those used for purposes of explanation), but also magnetic-based localization systems and hybrid impedance- and magnetic-based localization systems.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of sorting a plurality of electrophysiological signals measured by a respective plurality of electrodes carried by a multi-dimensional catheter, the method comprising:
   determining, via an electroanatomical mapping system, an orientation of the multi-dimensional catheter relative to a direction of interest;
   sorting, via the electroanatomical mapping system, the plurality of electrophysiological signals using the orientation of the multi-dimensional catheter relative to the direction of interest,
   wherein the direction of interest comprises a cardiac activation wavefront direction.

2. The method according to claim 1, further comprising the electroanatomical mapping system outputting a graphical representation of the sorted plurality of electrophysiological signals.

3. The method according to claim 1, wherein the determining, via the electroanatomical mapping system, the orientation of the multi-dimensional catheter relative to the direction of interest comprises the electroanatomical mapping system generating a graphical user interface and receiving a user selection of the orientation through the graphical user interface.

4. The method according to claim 3, wherein the graphical user interface comprises an orientation selection wheel.

5. The method according to claim 3, wherein the graphical user interface comprises an orientation selection slider.

6. The method according to claim 3, wherein receiving the user selection of the orientation through the graphical user interface comprises receiving the user's definition of a presumed cardiac activation wavefront direction through the graphical user interface.

7. The method according to claim 6, wherein receiving the user's definition of the presumed cardiac activation wavefront direction through the graphical user interface comprises receiving the user's definition of the cardiac activation wavefront direction on a geometric model of a heart.

8. The method according to claim 3, further comprising outputting a graphical representation of the user selection of the orientation on a geometric model of a heart.

9. The method according to claim 1, wherein the determining, via the electroanatomical mapping system, the orientation of the multi-dimensional catheter relative to the direction of interest comprises the electroanatomical mapping system determining the cardiac activation wavefront direction from the plurality of electrophysiological signals.

10. The method according to claim 1, wherein the sorting, via the electroanatomical mapping system, the plurality of electrophysiological signals using the orientation of the multi-dimensional catheter relative to the direction of interest comprises:

computing, via the electroanatomical mapping system, a rotation matrix using the orientation of the multi-dimensional catheter relative to the direction of interest;

applying the rotation matrix, via the electroanatomical mapping system, to a respective plurality of positions of the plurality of electrodes;

sorting the plurality of electrophysiological signals according to the respective plurality of positions of the plurality of electrodes after applying the rotation matrix thereto.

11. A system for sorting a plurality of electrophysiological signals measured by a respective plurality of electrodes carried by a multi-dimensional catheter, comprising:
a sorting and visualization module configured to:
determine, using information received by an electroanatomical mapping system, an orientation of the multi-dimensional catheter relative to a direction of interest; and
sort the plurality of electrophysiological signals using the orientation of the multi-dimensional catheter relative to the direction of interest,
wherein the direction of interest comprises a cardiac activation wavefront direction.

12. The system according to claim 11, further comprising a user interface module configured to receive as input a user selection of the orientation through a graphical user interface.

13. The system according to claim 12, wherein the graphical user interface comprises a geometric model of a heart.

* * * * *